United States Patent
Den et al.

(10) Patent No.: US 8,344,328 B2
(45) Date of Patent: Jan. 1, 2013

(54) THREE-DIMENSIONAL RADIATION POSITION DETECTOR

(75) Inventors: Toru Den, Tokyo (JP); Tatsuya Saito, Kawasaki (JP); Nobuhiro Yasui, Yokohama (JP); Ryoko Horie, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/213,393

(22) Filed: Aug. 19, 2011

(65) Prior Publication Data

US 2012/0049073 A1 Mar. 1, 2012

(30) Foreign Application Priority Data

Aug. 30, 2010 (JP) .................................. 2010-192397

(51) Int. Cl.
*G01T 1/20* (2006.01)

(52) U.S. Cl. ...................... 250/367; 250/361 R; 250/368
(58) Field of Classification Search .................. 250/367, 250/368, 361 R See application file for complete search history.

(56) References Cited

U.S. PATENT DOCUMENTS

| | | | | |
|---|---|---|---|---|
| 6,841,783 | B2 * | 1/2005 | Malmin | 250/368 |
| 7,276,705 | B2 * | 10/2007 | Leppert | 250/367 |
| 7,932,497 | B2 * | 4/2011 | Laurence et al. | 250/363.04 |
| 2005/0023733 | A1 * | 2/2005 | Burr | 264/400 |

FOREIGN PATENT DOCUMENTS

| | | |
|---|---|---|
| JP | 11-142524 A | 5/1999 |
| JP | 2006-522925 A | 10/2006 |

* cited by examiner

*Primary Examiner* — David Porta
*Assistant Examiner* — Mindy Vu
(74) *Attorney, Agent, or Firm* — Canon U.S.A., Inc. IP Division

(57) ABSTRACT

A position detector includes a photodetector having photodetecting elements; and a scintillator crystal having uniaxial optical anisotropy. The scintillator crystal is continuous in a uniaxial direction, is disposed on the photodetector such that the uniaxial direction is not perpendicular to the normal to a photodetecting surface, and has a length at least three times the pitch of the photodetecting elements. The uniaxial anisotropy allows at least 4% of scintillation light emitted from a region farthest above the photodetecting surface to reach the photodetecting elements, and allows from 4% to 35% of scintillation light emitted from a region closest to the photodetecting surface to reach the photodetecting elements.

4 Claims, 9 Drawing Sheets

THREE-DIMENSIONAL RADIATION POSITION DETECTOR

BACKGROUND OF THE INVENTION

1. Field of the Invention

The present invention relates to radiation detectors utilizing scintillators, and, more specifically, it relates to radiation detectors capable of collecting three-dimensional data.

2. Description of the Related Art

Positron emission tomography (PET) is a nuclear medicine imaging technique that has been employed to diagnose cancer, scan brain functions, and the like using images. In PET, a drug labeled with a radioactive isotope that emits positrons is injected into a subject, and two photons (gamma rays) emitted exactly in opposite directions after positron annihilation are simultaneously counted with a detector portion disposed around the subject. Thus, the position of a radiation source is specified to form an image. In the detector portion, detection units each including a photomultiplier tube (PMT) and a scintillator crystal disposed thereon are arranged in a circle. Examples of the scintillator crystal include $Bi_4Ge_3O_{12}$ (BGO) and $Lu_2SiO_5$ (LSO).

In conventional PET systems, the resolution decreases at the edge of the field of view. As shown in FIG. 1, gamma rays 11 generated at the center of the field of view (circle) are perpendicularly incident on scintillator crystals 12, whereas gamma rays 13 generated at an edge of the field of view are obliquely incident on the scintillator crystals 12. This causes a detection position error (parallax error) due to the length (height) of the scintillator crystals. To counter this, DOI-PET, a technique for suppressing the parallax error by identifying the information of the light-emitting position in the scintillator in the depth direction (depth of interaction; DOI) is drawing attention as a next-generation technique.

Japanese Patent Application Publication No. 2006-522925 (JP 2006522925), also published as WO 2004090572, discloses a method of identifying depth of interaction (DOI), in which a continuous scintillator crystal is disposed on a position-sensitive PMT (PS-PMT). In JP 2006522925, DOI is calculated from the difference in the diffusion of the scintillation light according to the depth of the light-emitting position. Another known method uses multi-layer detection units in which a plurality of scintillator crystals are disposed on a PS-PMT, on which layers of the scintillator crystals are stacked. Japanese Patent Laid-Open No. 11-142524 (JP 11142524) discloses an exemplary method in which DOI is identified by controlling the distribution of scintillation light with the presence/absence and positions of reflective members disposed between the scintillator crystals.

However, in a method using a continuous scintillator crystal, because the scintillation light is propagated isotropically in the crystal, the scintillation light is diffused over a wide area in the PS-PMT. Therefore, to identify the difference in the diffusion of the scintillation light according to the difference in depth of the light-emitting position, information has to be collected from a large number of detection pixels in the PS-PMT. If the depth of the light-emitting position is estimated by the calculation of a few pixels, the error increases.

In contrast, with the method in which layers of scintillator crystals are stacked, the depth of the light-emitting position can be estimated by the calculation of a few pixels. However, a very large number, for example, 120,000 scintillator crystals are required for each system. In addition, because reflective members have to be selectively disposed between the scintillator crystals, a process of assembling the detection units is very complex.

SUMMARY OF THE INVENTION

The present invention provides a three-dimensional radiation position detector capable of estimating the depth of the light-emitting position by the calculation of a few pixels and capable of easily assembling a detection unit from a small number of scintillator crystals, without reflective members.

The present invention provides a three-dimensional radiation position detector including: a photodetector having a plurality of photodetecting elements; and a scintillator crystal having such an optical anisotropy that the optical property in a first direction is different than in other directions, the scintillator crystal being continuous in the first direction and disposed on a photodetecting surface of the photodetector such that the first direction of the scintillator crystal is not perpendicular to the direction normal to the photodetecting surface of the photodetector. The scintillator crystal has a length, in the first direction, of at least three times the arrangement pitch of the plurality of photodetecting elements. The optical anisotropy is such that at least 4% of scintillation light emitted from a region immediately above and farthest from the photodetecting elements is allowed to reach the photodetecting elements, while from 4% to 35% of scintillation light emitted from a region immediately above and closest to the photodetecting element is allowed to reach the photodetecting element.

The present invention provides a three-dimensional radiation position detector capable of estimating a light-emitting position of the scintillation light by the calculation of a small number of photodetecting elements (pixels) and capable of easily assembling a detection unit from a small number of scintillator crystals, without reflective members.

Further features of the present invention will become apparent from the following description of exemplary embodiments with reference to the attached drawings.

DESCRIPTION OF THE EMBODIMENTS

Embodiments of the present invention will be described below. In a three-dimensional radiation position detector of the present invention, a scintillator crystal, which has an optical anisotropy such that the optical property in a first direction is different than in other directions and is continuous in the first direction, is disposed on a photodetecting surface of a position-sensitive photodetector. Examples of the position-sensitive photodetector include a position-sensitive PMT (PS-PMT) and a position-sensitive avalanche photodiode. Any type of the photodetector may be used, as long as it has a spatial resolution of several millimeters or less, and more preferably, 5 mm or less. Furthermore, a quick-response detector is desirable to count radiation rays to judge the coincidence. Of course, the emission decay time of the scintillator crystal, due to irradiation with radiation, is preferably 500 nsec or less, and more preferably, 50 nsec or less. In the following description, the photodetecting elements of the photodetector may also be called "pixels" or "light-receiving portions".

Next, a scintillator crystal of the present invention will be described.

Figure 1:
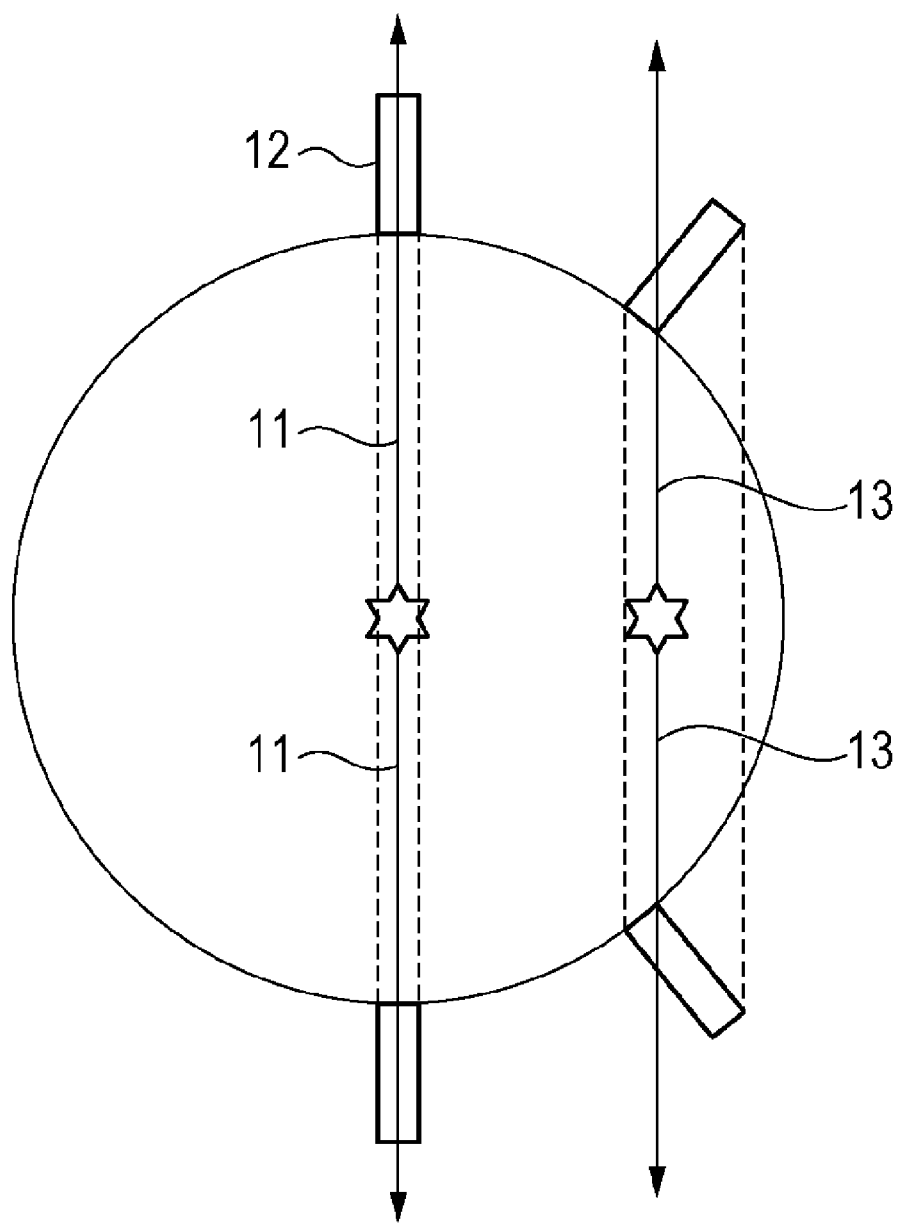
FIG. 1 is a diagram showing a parallax error occurring in a conventional PET system.
Figure 2:
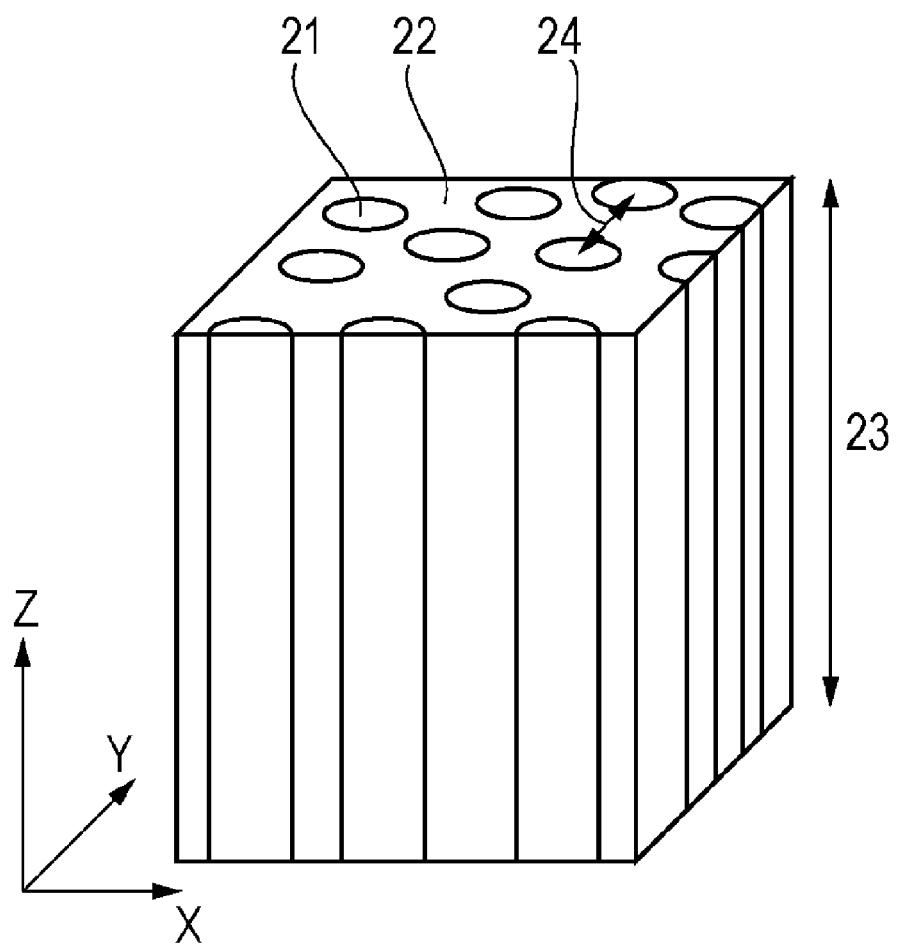
FIG. 2 is a schematic view of a scintillator crystal of the present invention.

A scintillator crystal in accordance with the present invention has a phase separation structure. Specifically, as shown in FIG. 2, a scintillator crystal includes a first crystal phase 21 composed of plural columnar crystals extending in a first direction (in FIG. 2, in a Z-axis direction) and a second crystal phase (matrix) 22. In the present embodiment, the first crystal phase 21 is composed of cylindrical columnar crystals that are present (embedded) within a three-dimensional crystal matrix referred herein as the second crystal phase 22. The first crystal phase 21 is not limited to cylindrical columnar crystals, but it can be implemented as hexagonal, triangular or any other polygonal columnar crystal embedded in the matrix. The second crystal phase 22 (matrix) is made of a material that emits light in a predetermined wavelength range upon excitation with radiation of a predetermined energy. Preferably, the second crystal phase 22 has a refractive index higher than the refractive index of the first crystal phase 21. A scintillator crystal formed in this manner results in a crystal having anisotropic optical properties. That is, a scintillator crystal of this type has such an optical anisotropy that the optical property in the first direction is different than the optical property in other directions.

An example of the scintillator crystal is a crystal that has a continuous phase in the first direction and has a phase separation structure in a direction orthogonal to the first direction. In other words, the scintillator crystal as shown in FIG. 2 has a phase separation structure, in which the first crystal phase containing a plurality of crystal columns extending in the first direction is present (embedded) in the second crystal phase. The second crystal phase having a refractive index higher than the refractive index of first crystal phase. In the following description, such an optical anisotropy that the optical property in the first direction is different than in other directions may be simply called a "uniaxial optical anisotropy". Accordingly, the first direction may be described as a "uniaxial direction". In this embodiment, the phase separation structure is formed when a uniform liquid state, in which constituent materials are fused and no structure is present, is transformed to a coagulate state, simultaneously crystallizing two crystal phases having a certain periodicity. The cross-section of the columnar crystals constituting the first crystal phase 21 is not limited to circular, oval, or rectangular, but may be any polygonal shape having several crystal surfaces. Furthermore, it is desirable that a scintillator crystal having such structure and size that it provides many columnar crystals on one detection pixel of the photodetector be used when a scintillator crystal and a photodetector is combined. Therefore, the diameter of the columnar crystals is preferably from 50 nm to 30 μm, and more preferably, from 200 nm to 10 μm. A period 24 (distance from center to center which may also be referred to as "pitch") of the columnar crystals of the first crystal phase is preferably from 500 nm to 50 μm, and more preferably, from 1 μm to 20 μm. Herein, the size ranges of the structures are determined by the selection of the material system and fabrication conditions, and the tendency will be described below. The scintillator crystal should have a height 23 sufficient to absorb radiation of a predetermined energy. For example, for a scintillator crystal to absorb 511 keV gamma rays the height 23 is usually about 30 mm, although it should be noted that the height depends on the material system. Although columnar crystals should extend in straight lines in the height direction, those having bent portions (non-straight portions), broken portions, branched or fused portions, and with various diameters may also be used.

Figure 3:
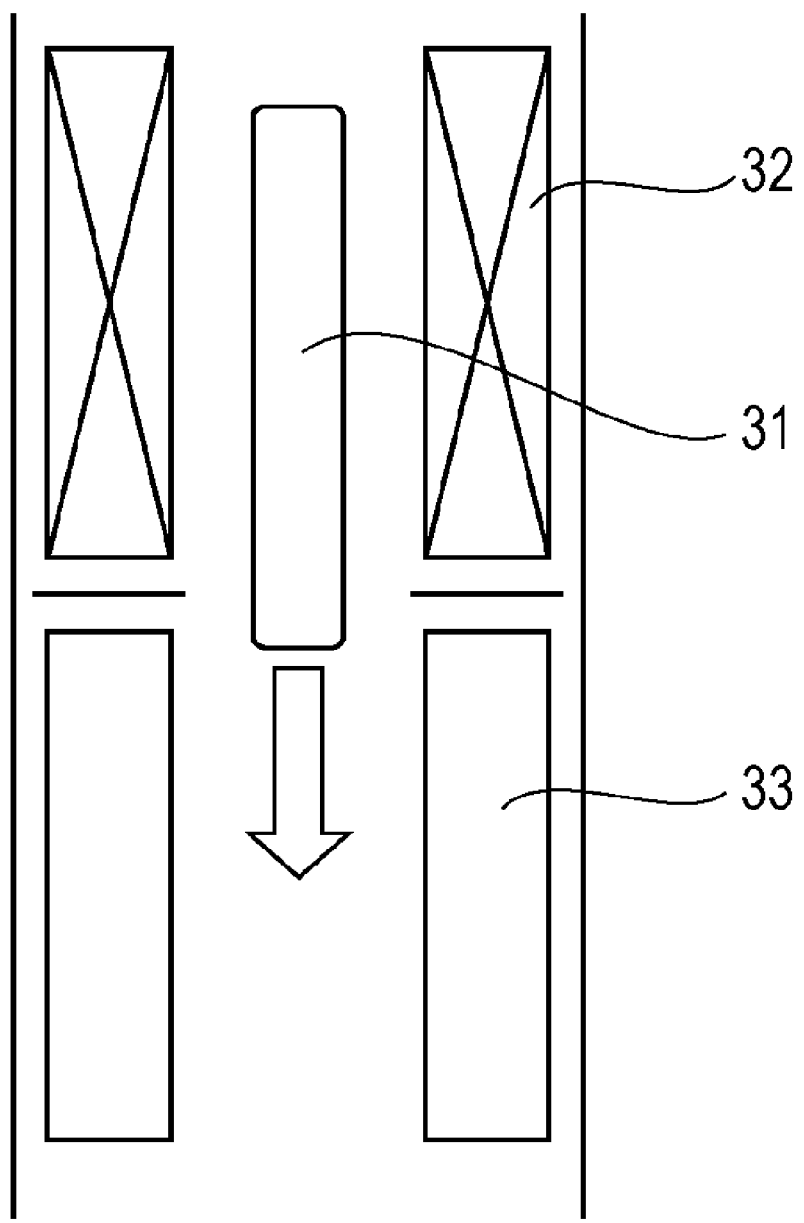
FIG. 3 is a schematic view showing an example of an apparatus for coagulating by providing unidirectional characteristics.

Next, a method of fabricating a scintillator crystal having the above-described phase separation structure will be described. Herein, the first crystal phase is composed of NaCl, and the second crystal phase is composed of CsI. First, NaCl is mixed with CsI with the composition at the eutectic point. Then, the mixture is heated to be fused and then cooled so as to be coagulated in a specific direction (such that the coagulation progresses in the specific direction). Herein, the eutectic point is a point at which the eutectic reaction occurs in an equilibrium diagram and at which two types of solid solutions are simultaneously produced from a liquid phase, thereby completing the coagulation. As a result of differential thermal analysis (DAT) and the like, the inventors herein have found that, in order to obtain the above-described structure, the eutectic composition and eutectic temperature for NaCl and CsI are NaCl:CsI=30:70 mol % and 490° C., respectively. To make coagulation progress in the specific direction, for example, as shown in FIG. 3, a sample 31 sealed in a cylindrical silica tube or the like to prevent oxidization of the material is disposed vertically, and a heater 32 or the sample 31 is moved at a substantially constant speed. At this time, it is important to control the temperature gradient and the moving speed so as to flatten the solid-liquid interface. In the present embodiment, suitable conditions are a temperature gradient of 30° C./mm or more and a moving speed of 850 mm/h or less. Furthermore, to ensure sufficient temperature gradient, a water-cooling portion 33 may be provided. In this embodiment, when melt of the sample, which is NaCl and CsI mixed at the eutectic composition, having a temperature of 500° C. is moved at a moving speed of 10 mm/h so as to be coagulated, a scintillator crystal having a phase separation structure, as shown in FIG. 2, whose first crystal phase is composed of NaCl and second crystal phase is composed of CsI, was obtained. The diameter of the columns composed of CsI, the first crystal phase, was about 2 μm, and the period thereof was about 4 μm. However, as described above, these can be adjusted by changing the fabrication conditions. It is thought that the diameter and period of the first crystal phase of a phase-separation scintillator crystal depend on the coagulation rate of the sample, and, in particular, the period of columnar crystals has the following relationship; $\lambda^2 \cdot v$=constant, where $\lambda$ is the period, and $v$ is the coagulation rate. Accordingly, by controlling the moving speed to change the coagulation rate, the period (pitch) and the diameter of the columnar crystals can be adjusted. The term "period" as used herein means the average interval (distance) between the centers of the columnar crystals (cylinders).

The uniaxial optical anisotropy (the optical anisotropy in which the optical property in the first direction is different that the optical property in other directions) of an NaCl—CsI scintillator crystal formed as above will be described below. When radiation of a predetermined energy is incident on the NaCl—CsI scintillator crystal, CsI constituting the matrix is excited, thereby emitting scintillation light. Although in the NaCl—CsI scintillator crystal the scintillation light is initially emitted isotropically, the scintillation light is prevented from spreading in a horizontal (orthogonal) direction to some extent and is anisotropically propagated in a direction parallel to the NaCl cylinders. This effect is considered to occur because, since scintillation light isotropically generated in a medium having a high refractive index can be totally reflected at the interface with respect to a medium having a low refractive index depending on the angle of incidence, the uniaxial optical anisotropy is exhibited because of a component propagated while being trapped in the medium having a high refractive index by repeating total reflection. Specifically, since the NaCl cylinders having a refractive index of 1.55 are embedded in the CsI matrix having a refractive index of 1.78, the higher refractive index of the CsI matrix prevents light from diffusing (spreading) in the orthogonal direction; and instead, forces light to anisotropically spread along the length of the columnar crystal structure. Furthermore, in the NaCl—CsI scintillator crystal, unlike in an optical fiber, light is not trapped in the columnar crystals (cylinders), but in the matrix. Thus, although the light has a uniaxial optical anisotropy, the light is propagated along the length of the columnar crystal while spreading in the horizontal direction to some extent. Although NaCl, the cylinders, also generates scintillation light upon excitation with radiation, from the stand point of the light-emitting efficiency and the radiation-absorbing efficiency, the light emission from CsI is dominant in the light emission from the NaCl—CsI scintillator crystal. Accordingly, the optical propagation characteristics may be discussed based only on the light emission from CsI constituting the matrix.

Figure 4A:
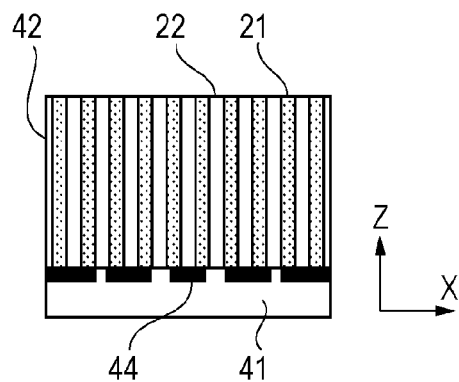
FIGS. 4A to 4D are schematic views showing diffusion of scintillation light incident on a photodetector.
Figure 4C:
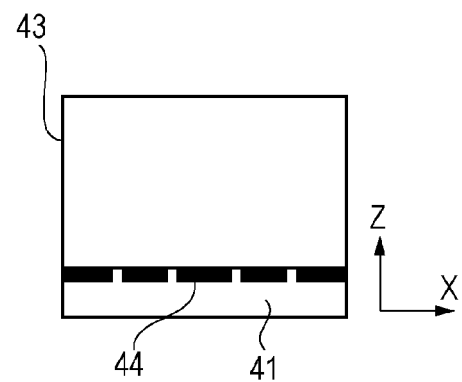
Figure 4B:
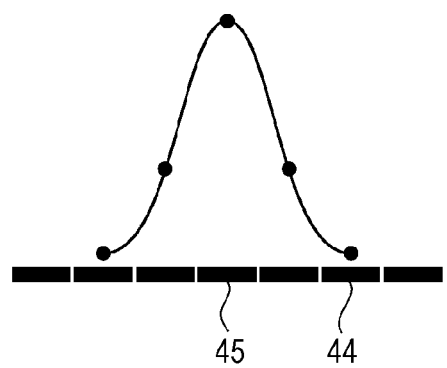
Figure 4D:
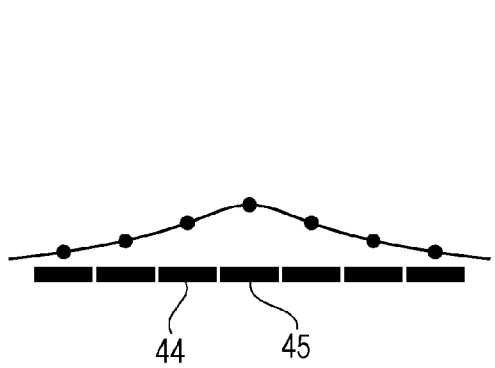

FIG. 4A shows the structure in which an NaCl—CsI scintillator crystal 42 having an uniaxial optical anisotropy, as shown in FIG. 2, is disposed on the photodetecting surface of a position sensitive PMT (PS-PMT) 41 such that the uniaxial direction and the direction normal to the photodetecting surface do not intersect perpendicularly. More specifically, for example, the uniaxial direction (first direction, Z in FIG. 4A) and the direction normal to the photodetecting surface are parallel to each other. In other words, the normal to the photodetecting surface and the uniaxial direction lay along a same plane). FIG. 4C is a diagram showing a CsI scintillator crystal 43 disposed on the PS-PMT 41. FIGS. 4B and 4D are schematic views showing the diffusion of scintillation light incident on the detection pixels 44 in the cases of FIGS. 4A and 4C, respectively. In both FIGS. 4A and 4C, the length (the height or depth, the length in direction Z in FIG. 2) of the scintillator is at least three times the arrangement pitch of the pixels 44, serving as the photodetecting elements. As shown in FIGS. 4C and 4D, because the scintillation light is propagated isotropically in the CsI scintillator crystal, the quantity of light incident on a detection pixel 45 immediately below the light-emitting position is small, and the diffusion occurs in a very wide area. Therefore, information from a large number of detection pixels is needed to identify the light-emitting position in the in-plane direction (the light-emitting position in the directions X and Y in FIG. 2) from the center of gravity of the diffusion of the emitted light, and to identify the depth of the light-emitting position (the light-emitting position in the direction Z in FIGS. 2 and 4A to 4D) from the condition of diffusion. Moreover, because the quantity of light incident on the detection pixels is small, the error increases.

In contrast, as shown in FIGS. 4A and 4B, because the scintillation light is propagated anisotropically in the NaCl—CsI scintillator crystal, the diffusion area of the scintillation light incident on the detection pixels is narrower than that of the CsI scintillator crystal. That is, because the difference in the quantity of incident light between adjacent pixels is large, the light-emitting position in the in-plane direction can be identified from a small number of detection pixels, and the position-identification error can be reduced because the quantity of light incident on the detection pixel immediately below the light-emitting position is large. As long as the signal strength ratio of the pixel immediately below the light-emitting position to the pixel next to it is at least 3:1, the light-emitting position in the in-plane direction can be identified from a few pixels, serving as photodetecting elements, as in the present invention. This condition can be rephrased using the extent of collected light: when an n-th position in the depth direction (position=1, 2, 3, . . . n-th, from the photodetecting element) is to be identified, the strength of the optical anisotropy should be such that, when scintillation light is emitted from the center of the n-th region farthest from that pixel, at least 4% of the total quantity of emitted light is incident on the pixel immediately below the light-emitting position. This condition applies to the case where all the surfaces, except for one in contact with the position detector, of the crystal serve as light-absorbing surfaces, not to the case where they serve as reflective surfaces or diffusing surfaces.

Furthermore, as described above, because light is trapped in the matrix in the NaCl—CsI scintillator crystal, the scintillation light is diffused orthogonally to some extent while being propagated along the columnar crystals, even though it has a uniaxial optical anisotropy. When the uniaxial optical anisotropy is too strong, the scintillation light is propagated almost with no diffusion, and thus, the difference in the quantity of light incident on the detection pixel immediately below the light-emitting position according to the difference in depth of the light-emitting position is insignificant. Herein, the depth of the light-emitting position means the light-emitting position in the direction Z in FIGS. 4A and 4C. Thus, in a scintillator having a uniaxial anisotropy, the depth direction is the uniaxial direction. In contrast, in NaCl—CsI scintillator crystals, because scintillation light is diffused to some extent while being propagated, the difference in the quantity of light incident on the detection pixel immediately below the light-emitting position according to the difference in depth of the light-emitting position is significant enough, whereby the light-emitting position in the depth direction can be identified. Note that, when an n-th position in the depth direction (1, 2, 3, . . . n-th, from the photodetecting element) is to be identified, the n-th position can be identified as long as the difference in the quantity of light incident on the detection pixel immediately below the light-emitting position between the scintillation light emitted from the center of an L-th region ($2 \leq L \leq n$), in n number of regions, located vertically above the center of a pixel and the scintillation light emitted from the center of an L−1-th region is distinguishable. In particular, the n-th position can be identified as long as there is a difference of at least 10% in the quantity of incident light between the regions adjacent in the depth direction. In other words, the number of regions into which a scintillator having a uniaxial optical anisotropy (an optical anisotropy in which the optical property in the first direction is different than in other directions) is divided (i.e., the number of segmenting a region) in the uniaxial direction (first direction) may be defined such that there is at least 10% difference in the quantity of light incident on the pixel, serving as the photodetecting element, between regions adjacent in the uniaxial direction (first direction). More preferably, the difference in the quantity of incident light is at least 25%. Note that, however, this applies only to the case where the quantity of light incident on the light-receiving portion, serving as the photodetecting element, is sufficient, not to the case where the quantity of incident light is very small.

Furthermore, in addition to the condition for identifying the light-emitting position in the depth direction, as a range in which the anisotropy is not too strong, in order to enable the light-emitting position in the in-plane direction of the detector to be identified from a few pixels as in the present invention, it is essential to make the signal strength ratio of the pixel immediately below the light-emitting position to the pixel next to it 20:1 or less, when scintillation light is emitted from the center of the region closest to the light-receiving portion. In other words, the strength of the optical anisotropy may be set such that the quantity of light incident on the pixel immediately below the light-emitting position is 35% or less of the total quantity of emitted light, when light is emitted from the center of the region closest to the light-receiving portion. This condition applies to the case where all the surfaces, except for one in contact with the position detector, of the crystal serve as light-absorbing surfaces, not to the case where they serve as reflective surfaces or diffusing surfaces.

As has been described, with the present invention, the light-emitting position can be identified in three dimensions by calculating the information from a few pixels. The condition of the uniaxial optical anisotropy (the strength of the optical anisotropy) for achieving this is that at least 4% of the scintillation light emitted from a region of the scintillator immediately above and farthest from the photodetecting element, constituting the pixel, is allowed to reach the photodetecting element immediately therebelow, while from 4% to 35% of the scintillation light emitted from a region closest to the photodetecting element is allowed to reach the photodetecting element immediately therebelow.

Although this embodiment has been described taking an NaCl—CsI scintillator crystal as an example, the present invention is not limited to this material system, and any material that achieves the above-described optical anisotropy may be used. Furthermore, in material systems having a phase separation structure, a combination in which a material having a low refractive index constitutes the matrix and a material having a high refractive index constitutes the cylinders, unlike NaCl—CsI system, is possible. In such a case, because light totally reflected in the cylinders is not diffused at all, the above optical anisotropy can be achieved by selecting material systems with a refractive index ratio relatively close to 1 and a relatively high reflectance between phases.

As has been described, in order to adjust the uniaxial optical anisotropy to an intended strength, in the present invention, it is essential to appropriately select the refractive index ratio and reflectance at the interface of two phases, the period of the cylinder, and the area ratio (volume ratio) between two phases in the phase-separation scintillator crystal.

As has been described, with the three-dimensional radiation position detector of the present invention, the light-emitting position in the in-plane and depth directions can be identified from the information of the quantity of light received by a few pixels. Furthermore, because there is no need to use layers of scintillator crystals or reflective members, a detection unit can be easily assembled from a small number of scintillator crystals and at low cost.

Example

In this example, with respect to a scintillator crystal having a phase separation structure, the difference in the quantity of light incident on a detection pixel according to the refractive index ratio between two phases was calculated using geometrical and optical simulation.

Figure 5:
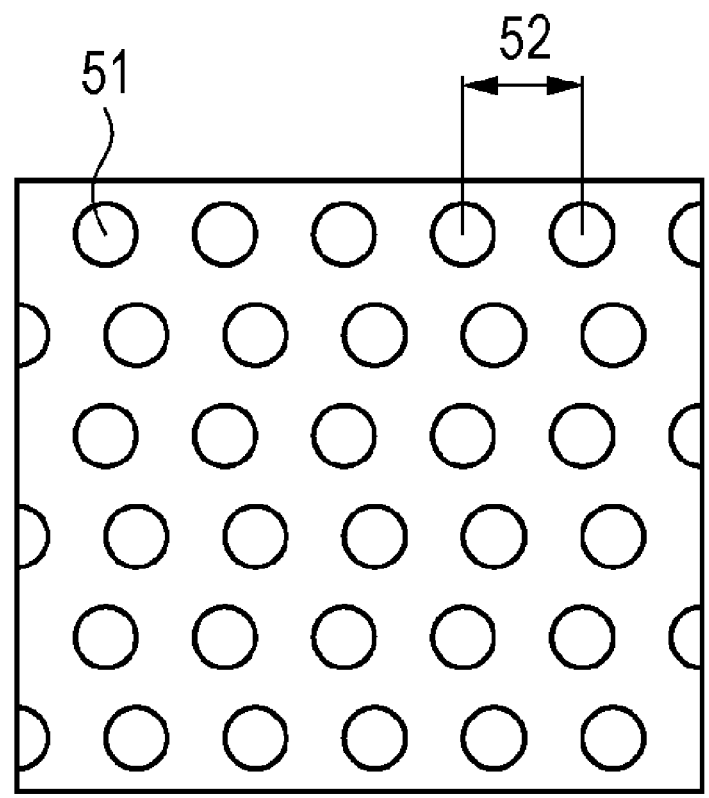
FIG. 5 is a diagram showing the structure of a phase separation scintillator.

Calculation was performed based on an assumption that, a detection pixel of an actual detection unit has a size of 3 mm×3 mm and a scintillator crystal has a height of 30 mm, which were multiplied by 1/9 to reduce the calculation load. More specifically, a phase-separation scintillator crystal having a height of 3333 μm was disposed on a photodetector, whose pixel size (the size of the photodetecting element) was 333 μm×333 μm. The structure of the phase separation scintillator was a triangular grid array, as shown in FIG. 5, in which the diameter of a cylinder 51 was 2 μm, and a period 52 was 4 μm. The calculation was performed based on an assumption that all the surfaces, except for one in contact with the photodetector's surface, of the phase-separation scintillator crystal were absorption surfaces.

Figure 6:
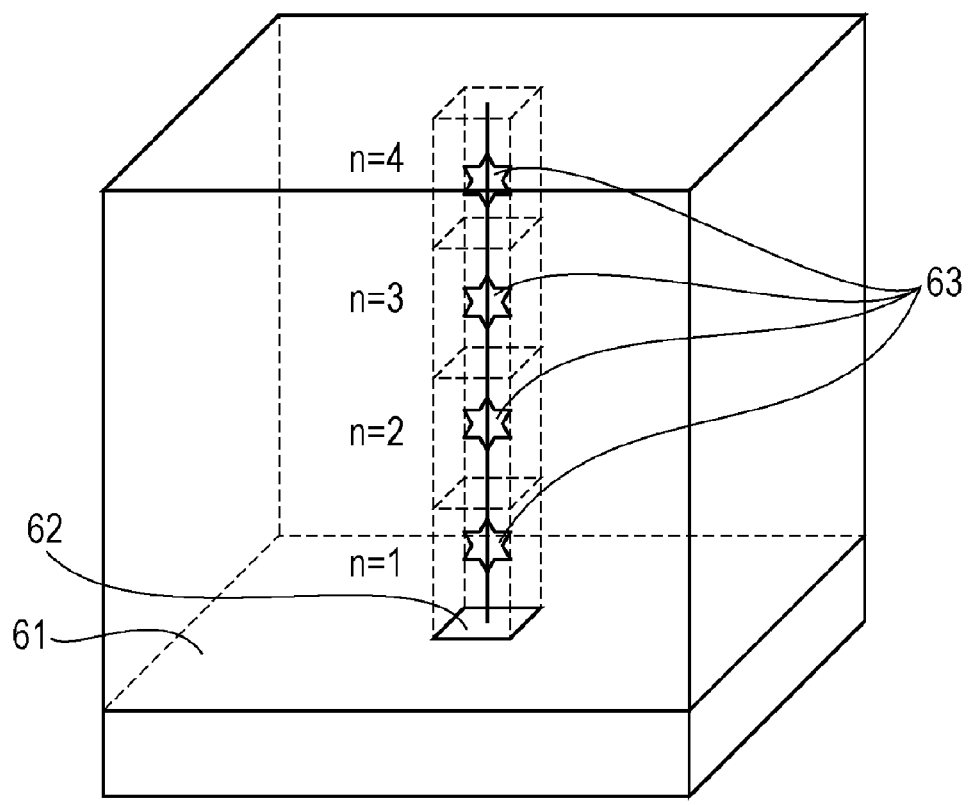
FIG. 6 is a diagram showing the light-emitting position of the phase separation scintillator.

In an example, the depth of the light-emitting position to be identified was divided into four levels (n=4). The light-receiving ratio of the pixel immediately below the light-emitting position to the pixel adjacent thereto was calculated assuming that light (scintillation light) 63 was emitted isotropically from a light source having a radius of 100 μm, at the center (417 μm, 1250 μm, 2083 μm, and 2917 μm from the photodetecting surface 61) of each n region located vertically above the center of a pixel 62 on a photodetecting surface 61 of the photodetector, as shown in FIG. 6. The "light-receiving ratio" as used herein means the proportion of the quantity of light incident on each pixel in the total quantity of emitted light, represented in percentage. Table 1 shows the calculation results for the case where the refractive index of the cylinder medium is 1.00, while the refractive index of the matrix medium is varied. Because only the refractive index ratio has an influence on the results, the refractive index of the cylinder was set to 1.00 for the convenience's sake. Table 1 also includes the calculation results for a single-crystal scintillator having no phase separation structure, for the purpose of comparison.

TABLE 1

| | | refractive index of matrix medium | 1.04 | 1.23 | 1.42 | 1.78 | 2.00 | single crystal |
|---|---|---|---|---|---|---|---|---|
| light-receiving ratio | 2917 μm | pixel next to light-emitting position | 1.228 | 1.457 | 1.580 | 1.608 | 1.581 | 0.102 |
| | | pixel immediately below light-emitting position | 4.155 | 8.119 | 9.123 | 10.483 | 10.570 | 0.104 |
| | | pixel diagonal to light-emitting position | 0.638 | 0.608 | 0.607 | 0.570 | 0.537 | 0.101 |
| | 2083 μm | pixel next to light-emitting position | 1.758 | 1.841 | 1.901 | 1.885 | 1.847 | 0.195 |
| | | pixel immediately below light-emitting position | 5.934 | 10.912 | 13.000 | 14.321 | 14.500 | 0.203 |
| | | pixel diagonal to light-emitting position | 0.875 | 0.756 | 0.704 | 0.631 | 0.596 | 0.189 |

TABLE 1-continued

| refractive index of matrix medium | | 1.04 | 1.23 | 1.42 | 1.78 | 2.00 | single crystal |
|---|---|---|---|---|---|---|---|
| 1250 μm | pixel next to light-emitting position | 2.615 | 2.361 | 2.288 | 2.128 | 2.068 | 0.504 |
| | pixel immediately below light-emitting position | 9.374 | 15.567 | 18.428 | 20.510 | 20.924 | 0.558 |
| | pixel diagonal to light-emitting position | 1.180 | 0.905 | 0.805 | 0.676 | 0.624 | 0.461 |
| 417 μm | pixel next to light-emitting position | 3.615 | 2.735 | 2.336 | 1.921 | 1.792 | 2.411 |
| | pixel immediately below light-emitting position | 20.077 | 26.724 | 30.298 | 33.017 | 33.692 | 4.417 |
| | pixel diagonal to light-emitting position | 1.176 | 0.829 | 0.641 | 0.492 | 0.453 | 1.525 |

Figure 7:
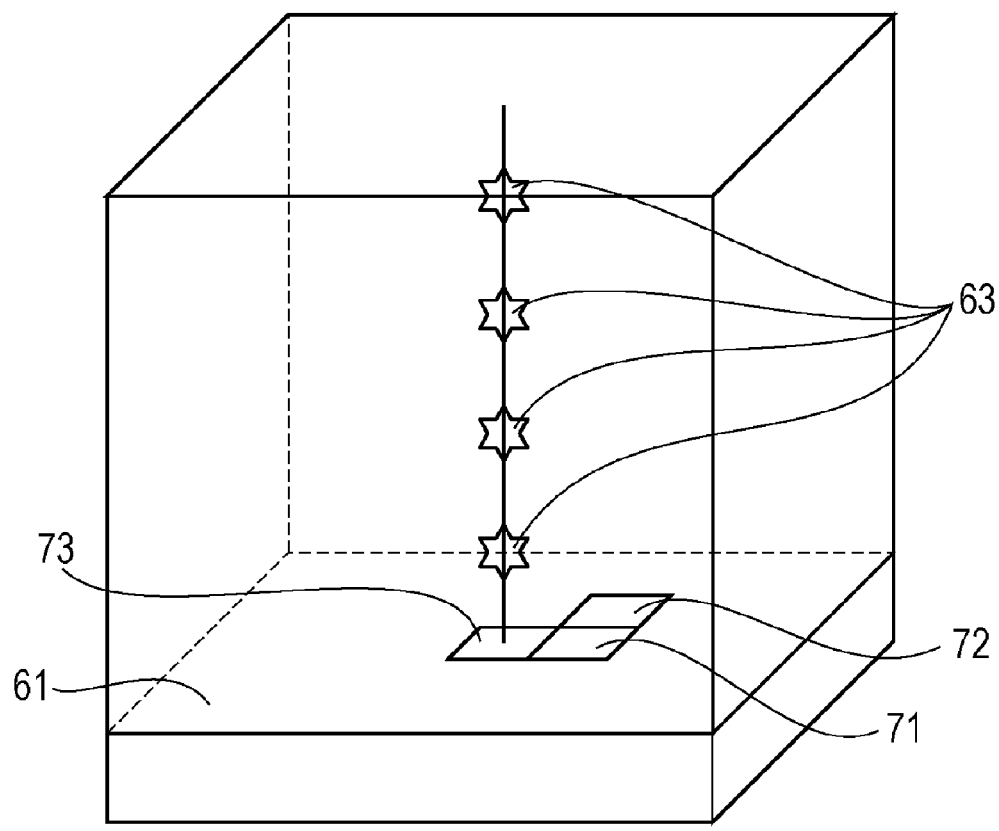
FIG. 7 is a schematic view of detection pixels on a photodetector surface.

In Table 1, "pixel next to light-emitting position" and "pixel diagonal to light-emitting position" refer to a pixel 71 and a pixel 72, respectively, which are adjacent to a pixel 73 immediately below the light-emitting position, as shown in FIG. 7. From the calculation results of Table 1, in a single-crystal scintillator having no phase separation structure, the light-receiving ratio of each detection pixel is very small. When the height of the light-emitting position from the photodetecting surface is 2917 μm, the light-receiving ratio of the pixel immediately below the light-emitting position is 0.104%, and the difference in the light-receiving ratio between the detection pixels is insignificant because the difference is caused only by the solid angle from the light-emitting position. Therefore, identifying the light-emitting position from the light-receiving ratio of the adjacent pixels is very difficult. In addition, at a height of 1250 μm or more, the difference in the light-receiving ratio of the pixel immediately below the light-emitting position according to the height of the light-emitting position from the photodetecting surface is 0.4% or less. Thus, identifying the depth of the light-emitting position is very difficult.

Figure 8:
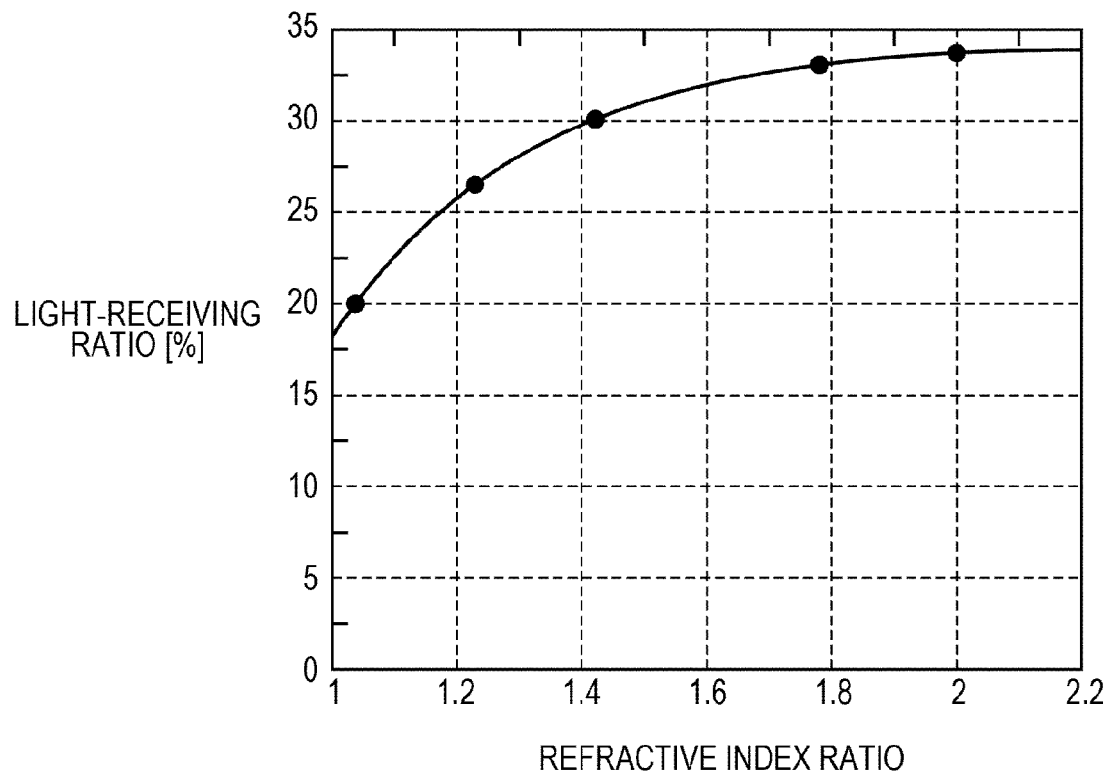
FIG. 8 is a graph of the light-receiving ratio of the pixel immediately below the light-emitting position versus the refractive index ratio between two phases.

In contrast, in a phase separation scintillator, even when the height of the light-emitting position from the photodetecting surface is 2917 μm, that is, even in a region farthest from the photodetecting surface, the light-receiving ratio of the pixel immediately below the light-emitting position is at least three times larger than the adjacent pixels. Thus, the light-emitting position can be identified from the light-receiving ratio of the adjacent pixels. This is proved by the fact that the light-receiving ratio of the pixel immediately below the light-emitting position is at least 4%. Because the quantity of light collected is larger than that of a single-crystal scintillator because of the uniaxial anisotropy of propagation of the emitted light, the calculation from adjacent pixels is enabled. In addition, the difference in the light-receiving ratio of the pixel immediately below the light-emitting position according to the height of the light-emitting position from the photodetecting surface is distinguishable because the difference is sufficient, i.e., more than 10%, although it depends on the refractive index ratio between two phases. Thus, the depth of the light-emitting position can be identified. FIG. 8 shows the light-receiving ratio of the pixel immediately below the light-emitting position versus the refractive index ratio between two phases, when the height of the light-emitting position from the photodetector's surface is 417 μm. This calculation is based on an assumption that all the surfaces, except for one in contact with the photodetector's surface, of the phase-separation scintillator crystal are absorption surfaces. Therefore, if whole light is collected by the pixel immediately below the light-emitting position, the light-receiving ratio is 50%. In contrast, from FIG. 8, when the height of the light-emitting position from the photodetector's surface is 417 μm, the light-receiving ratio of the pixel immediately below the light-emitting position is 35% or less. This shows that, in a phase separation scintillator, the scintillation light is propagated while being diffused to an extent conforming to the condition of the present invention, even though it has a uniaxial optical anisotropy. That is, this scintillator has such a light-collecting property (uniaxial optical anisotropy) that the proportion of the quantity of scintillation light emitted from a region closest to the photodetecting element (pixel), where the contrast in the light-receiving ratio with respect to the adjacent pixel is greatest, reaching the pixel to the scintillation light reaching a pixel adjacent to the aforementioned pixel is 20:1 or less. This means that the uniaxial optical anisotropy of the scintillator is not too strong. This also means that, from the inventors' study as described above, the scintillator has such an uniaxial optical anisotropy that no more than 35% of the scintillation light emitted in a region closest to the pixel, serving as the photodetecting element, is allowed to reach the pixel. Thus, the light-emitting position in the in-plane and depth directions can be specified by making the optical anisotropy of the scintillator located immediately above the photodetecting element, constituting the pixel, such that at least 4% of the scintillation light emitted from a region farthest from the photodetecting elements is allowed to reach the photodetecting element immediately therebelow, while from 4% to 35% of the scintillation light emitted from a region closest to the photodetecting element is allowed to reach the photodetecting element immediately therebelow. By making the scintillation light such that it is not diffused too much or focused too much, it is possible to provide sufficient contrast in the light-receiving ratio between the adjacent pixels, serving as the photodetecting elements, and a sufficient difference in the quantity of incident light between adjacent regions in the depth (height) direction. As a result, the light-emitting position can be specified in the in-plane and depth (height) directions.

Table 2 shows the number of photons incident on each pixel, estimated using the results shown in Table 1. That is, the number of photons incident on each pixel, when a 511 keV photon is incident on a phase-separation scintillator crystal and a single-crystal scintillator, generating photons having a scintillation light energy according to light yield, was calculated. Herein, "light yield" means the number of photons generated upon excitation of a scintillator with a single 1 MeV photon, and it is used as an index of the intensity of emitted light of the scintillator. In this example, calculation was performed using a light yield of 33000 ph/MeV for a cerium-doped LSO scintillator used in PET.

TABLE 2

| | | refractive index of matrix medium | 1.04 | 1.23 | 1.42 | 1.78 | 2.00 | single crystal |
|---|---|---|---|---|---|---|---|---|
| number of photons | 2917 μm | pixel next to light-emitting position | 207.01 | 245.74 | 266.49 | 271.22 | 266.55 | 17.12 |
| | | pixel immediately below light-emitting position | 700.70 | 1369.15 | 1538.45 | 1767.75 | 1782.30 | 17.57 |
| | | pixel diagonal to light-emitting position | 107.53 | 102.56 | 102.28 | 96.03 | 90.57 | 17.04 |
| | 2083 μm | pixel next to light-emitting position | 296.44 | 310.36 | 320.58 | 317.92 | 311.48 | 32.88 |
| | | pixel immediately below light-emitting position | 1000.71 | 1840.12 | 2192.79 | 2414.87 | 2444.72 | 34.23 |
| | | pixel diagonal to light-emitting position | 147.63 | 127.46 | 188.69 | 106.43 | 100.50 | 31.87 |
| | 1250 μm | pixel next to light-emitting position | 441.01 | 398.18 | 385.78 | 358.81 | 348.68 | 84.95 |
| | | pixel immediately below light-emitting position | 1580.78 | 2625.08 | 3107.48 | 3458.58 | 3528.33 | 94.07 |
| | | pixel diagonal to light-emitting position | 198.96 | 152.65 | 135.80 | 113.94 | 105.23 | 77.77 |
| | 417 μm | pixel next to light-emitting position | 609.58 | 461.26 | 393.99 | 323.93 | 302.12 | 406.50 |
| | | pixel immediately below light-emitting position | 3385.62 | 4506.47 | 5109.07 | 5567.73 | 5681.47 | 744.82 |
| | | pixel diagonal to light-emitting position | 198.32 | 139.80 | 108.07 | 82.99 | 76.36 | 257.09 |

From Table 2, in the case of a single-crystal scintillator having no phase separation structure, the number of photons in each detection pixel is very small, and the difference in the number of photons between detection pixels is also insignificant. For example, at a light-emitting position of 2917 μm, the differences in the number of photons between the pixel immediately below the light-emitting position and the pixel next to it and between the pixel immediately below the light-emitting position and the pixel diagonal to it are 0.45 ph/pixel and 0.53 ph/pixel, respectively. Herein, "ph/pixel" means the number of photons detected by one pixel. Because the light emission and the light propagation in a crystal vary in an actual system, the light-emitting position cannot be identified from such a small difference. The difference in the number of photons in the pixel immediately below the light-emitting position according to the height of the light-emitting position from the photodetector's surface is 16.66 ph/pixel at 2917 μm and 2083 μm, which may be insufficient for identifying the depth of the light-emitting position. At a light-emitting position of 417 μm, the difference in the number of photons between the detection pixels is large, making it possible to identify the light-emitting position. However, because the resolution is very low when the light is emitted at a position far from the photodetector's surface in the height direction, it is difficult to identify the light-emitting position and depth only from the adjacent pixels. That is, in a scintillator crystal having no phase separation structure, the light-emitting position and depth can be identified from the adjacent pixels only when the thickness of the scintillator crystal is small (about three times the pixel size or less). However, taking into consideration the actual pixel size, namely, about 3 mm×3 mm, a scintillator crystal having a thickness of about 9 mm with such a high density and a high radiation absorption coefficient that it can absorb 511 keV gamma rays is needed, which is impractical.

Figure 9:
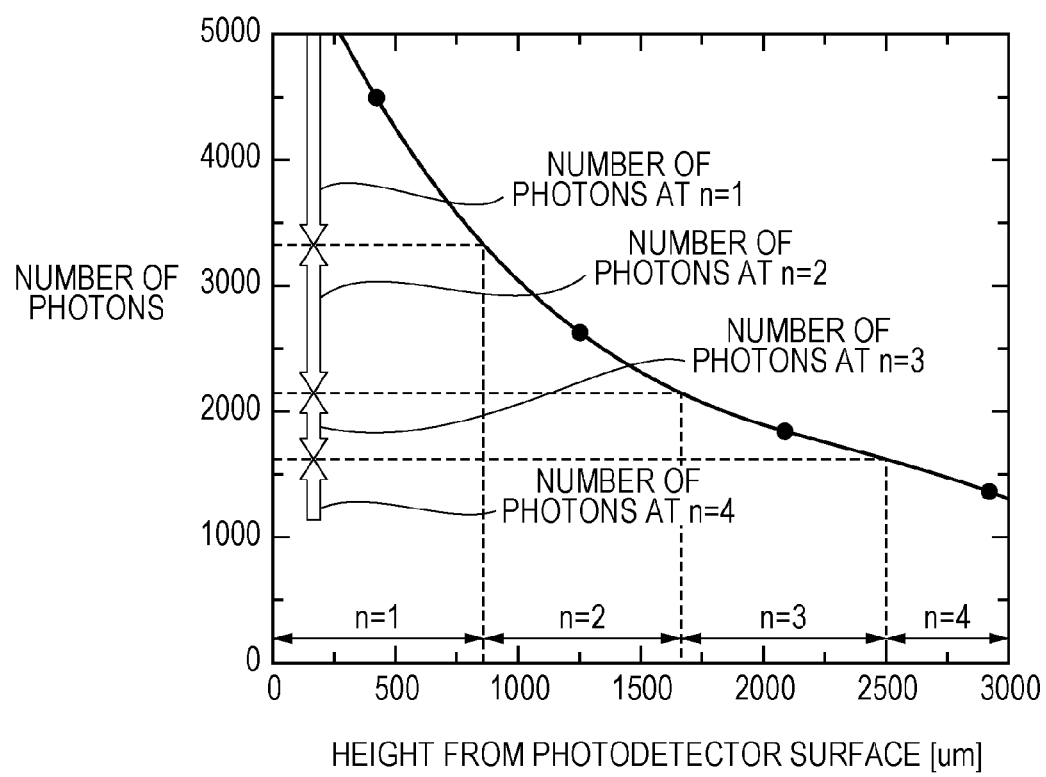
FIG. 9 is a graph of the number of photons at each depth of the light-emitting position.

In contrast, in the case of a phase separation scintillator, the number of photons incident on each pixel is large, and the differences in the number of photons between the pixel immediately below the light-emitting position and the pixel next to it and between the pixel immediately below the light-emitting position and the pixel diagonal to it are significant enough. Accordingly, the light-emitting position can be identified from the number of photons in adjacent pixels. Furthermore, because the difference in the number of photons incident on the pixel immediately below the light-emitting position according to the height of the light-emitting position from the photodetector's surface is significant enough, i.e., more than 10 times that of the single crystal, although it depends on the refractive index ratio between two phases, the depth of the light-emitting position can be identified. FIG. 9 shows a graph showing the number of photons incident on the pixel immediately below the light-emitting position versus the depth of the light-emitting position, when the matrix medium has a refractive index of 1.23, in Table 2. As shown in FIG. 9, by obtaining the output ranges that depend on the depth direction in advance, and by comparing them with the actual outputs, the depth of the light-emitting position can be identified.

Although the discussion in the example is based on an assumption that the light-emitting position in the depth direction is located at the center of a region, even when the light-emitting position is located at a peripheral portion off the center of the region, the pseudo-in-plane light-emitting position can be specified and the quantity of light emitted can be estimated by performing center-of-gravity calculation on several pixels near the pixel immediately below the light-emitting position. Accordingly, the light-emitting position in the depth direction can be identified without departing from the method of this example.

From the above results, with the three-dimensional radiation position detector of the present invention, the light-emitting position can be identified by comparing the output of the pixel immediately below the light-emitting position and that of the pixel adjacent thereto. In other words, the condition of the uniaxial optical anisotropy is such that at least 4% of the scintillation light emitted from a region of the scintillator immediately above and farthest from the photodetecting element, constituting the pixel, is allowed to reach the photodetecting element immediately therebelow, while from 4% to 35% of the scintillation light emitted from a region closest to the photodetecting element is allowed to reach the photodetecting element immediately therebelow. In addition, by comparing the output ranges that depend on the depth direction and obtained in advance with the actual outputs obtained from the pixel immediately below the light-emitting position, the depth of the light-emitting position can be identified.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-192397 filed Aug. 30, 2010, which is hereby incorporated by reference herein in its entirety.

What is claimed is:

1. A three-dimensional radiation position detector comprising:
   a photodetector having a plurality of photodetecting elements; and
   a scintillator crystal having an optical anisotropy such that an optical property in a first direction is different than in other directions, the scintillator crystal being disposed on a photodetecting surface of the photodetector such that the first direction of the scintillator crystal is not perpendicular to the direction normal to the photodetecting surface of the photodetector,
   wherein the scintillator crystal has a length, in the first direction, of at least three times the average pitch of the plurality of photodetecting elements, and
   wherein the optical anisotropy is such that at least 4% of scintillation light emitted from a region directly above and farthest from the photodetecting elements is allowed to reach the photodetecting elements, and 4% to 35% of scintillation light emitted from a region immediately above and closest to the photodetecting elements is allowed to reach the photodetecting elements.

2. The three-dimensional radiation position detector according to claim 1,
   wherein the scintillator crystal has a phase separation structure, in which a first crystal phase containing a plurality of columns extending in the first direction is embedded in a second crystal phase having a refractive index higher than the first crystal phase.

3. The three-dimensional radiation position detector according to claim 2, wherein the first crystal phase containing the plurality of columns is continuous in the first direction, and
   wherein the phase separation structure is formed in a direction orthogonal to the first direction.

4. The three-dimensional radiation position detector according to claim 1, wherein the optical property includes optical propagation within the scintillator, and wherein
   optical propagation in the first direction is higher than optical propagation in the other directions.

* * * * *